United States Patent [19]

Kakimoto et al.

[11] Patent Number: 5,041,577

[45] Date of Patent: Aug. 20, 1991

[54] ORGANOGERMANIUM COMPOUNDS, PROCESSES FOR PRODUCING THE SAME, AND AGENT FOR INHIBITING THE ACTIVITY OF OPIOID PEPTIDE-DEGRADING ENZYME

[75] Inventors: Norihiro Kakimoto; Toru Yoshihara, both of Tokyo, Japan

[73] Assignee: Asai Germanium Research Institute Co., Ltd., Tokyo, Japan

[21] Appl. No.: 468,670

[22] Filed: Jan. 23, 1990

[30] Foreign Application Priority Data

Jan. 30, 1989 [JP] Japan ................................. 1-20624

[51] Int. Cl.$^5$ ............................................ C07F 7/30
[52] U.S. Cl. ........................................ 556/87; 556/88; 556/90; 556/91; 556/104
[58] Field of Search ................... 556/87, 88, 104, 90, 556/91; 514/492

[56] References Cited

U.S. PATENT DOCUMENTS

| | | | |
|---|---|---|---|
| 4,207,245 | 6/1980 | Halbert | 556/28 |
| 4,271,084 | 6/1981 | Ishikawa et al. | 556/87 X |
| 4,501,702 | 2/1985 | Bulten et al. | 556/87 X |
| 4,730,064 | 3/1988 | Halbert et al. | 556/28 X |
| 4,937,338 | 6/1990 | Flohr et al. | 556/28 X |

FOREIGN PATENT DOCUMENTS

| | | |
|---|---|---|
| 61-267591 | 11/1986 | Japan . |
| 7308463 | 12/1974 | Netherlands . |
| 1408147 | 10/1975 | United Kingdom . |

Primary Examiner—Arthur C. Prescott
Attorney, Agent, or Firm—Armstrong, Nikaido, Marmelstein, Kubovcik & Murray

[57] ABSTRACT

The present invention relates to (a) novel organogermanium compounds represented by the general formula (1)

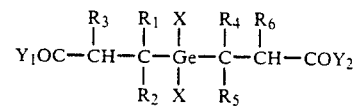

($R_1$ to $R_6$ are independently a hydrogen atom or a lower alkyl group; X is a halogen atom; and $Y_1$ and $Y_2$ are independently a hydroxyl group or a group chemically equivalent thereto) or by the general formula (2)

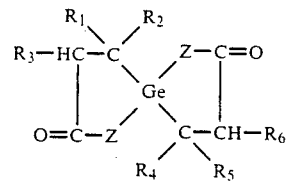

($R_1$ to $R_6$ are independently a hydrogen atom or a lower alkyl group, and Z is an oxygen atom or a sulfur atom), (b) processes for producing the above organogermanium compounds, and (c) an agent for inhibiting the activity of opioid peptide-degrading enzyme, containing the above organogermanium compounds as an active ingredient.

13 Claims, No Drawings

ORGANOGERMANIUM COMPOUNDS, PROCESSES FOR PRODUCING THE SAME, AND AGENT FOR INHIBITING THE ACTIVITY OF OPIOID PEPTIDE-DEGRADING ENZYME

FIELD OF THE INVENTION

The present invention relates to organogermanium compounds, processes for producing the same, and an agent for inhibiting the activity of opioid peptide-degrading enzyme.

BACKGROUND OF THE INVENTION

In recent years, study on organic compounds of germanium (a homologue of carbon) has actively been conducted, and many study results have been presented or published. Thus, attention is being paid to organogermanium compounds in various fields, particularly medical and pharmaceutical fields.

For example, it is reported that carboxyethylgermanium sesquioxide (Japanese Patent Publication No. 2498/1971) which is an organogermanium compound formed by bonding of a propionic acid derivative of germanium and oxygen atom at a 2:3 ratio shows a hypotensive action to spontaneous hypertensive rats, an amyloidosis-alleviating action, a macrophage-augmenting action, an interferon-inducing action, an antitumor action, etc. The above sesquioxide is in trial use clinically.

The above carboxyethylgermanium sesquioxide is a compound represented by a chemical formula $(Ge-CH_2-CH_2-COOH)_2O_3$ The so far developed organogermanium compounds are not restricted to the above compound alone and include cylic compounds represented by the following general formula.

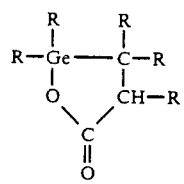

On the above cyclic compounds, patent application was made by Japanese Patent Application Kokai (Laid-Open) No. 267591/1986.

The above cyclic compounds contain a Ge atom as a ring-forming element. Since germanium atom is tetravalent, if there is developed an organogermanium compound of different chemical structure which contains a germanium atom in the form of, for example, a spiro-atom, it is highly possible that such an organogermanium compound find novel utility.

However, there has hitherto existed no organogermanium compound which contains a germanium atom in the form of a spiro-atom. Therefore, it has been desired to develop such an organogermanium compound and its useful application.

SUMMARY OF THE INVENTION

The present invention has been made to solve the drawbacks of the prior art.

The present invention provides, as the first organogermanium compound of the present invention, an organogermanium compound represented by the general formula (1)

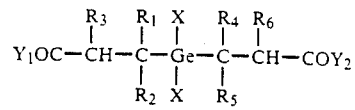

wherein $R_1$ to $R_6$ are independently a hydrogen atom or a lower alkyl group; X is a halogen atom; and $Y_1$ and $Y_2$ are independently a hydroxyl group or a group chemically equivalent thereto.

The present invention also provides, as the second organogermanium compound of the present invention, an organogermanium compound represented by the general formula (2)

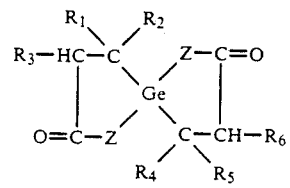

wherein $R_1$ to $R_6$ are independently a hydrogen atom or a lower alkyl group, and Z is an oxygen atom or a sulfur atom.

The present invention also provides, as a process (the first process of the present invention) for producing the first organogermanium compound of the present invention represented by the general formula (1), a process for producing an organogermanium compound represented by the general formula (1)

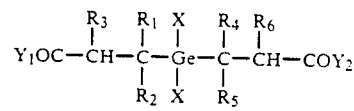

($R_1$ to $R_6$ are independently a hydrogen atom or a lower alkyl group; X is a halogen atom; and $Y_1$ and $Y_2$ are independently a hydroxyl group or a group chemically equivalent thereto), which process comprises reacting a compound represented by the general formula (3)

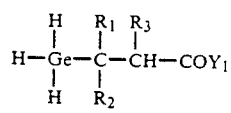

($R_1$ to $R_3$ and $Y_1$ have the same definitions as given above) with a halogen $X_2$ to obtain a dihalide compound represented by the general formula (4)

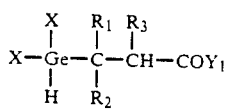

($R_1$ to $R_3$ and $Y_1$ have the same definitions as given above, and X is a halogen atom) and reacting the dihalide compound (4) with an unsaturated compound represented by the general formula (5)

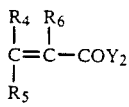

(R4 to R6 and Y2 have the same definitions as given above) to obtain an organogermanium compound represented by the general formula (1) shown above.

The present invention also provides, as a process (the second process of the present invention) for producing the second organogermanium compound of the present invention represented by the general formula (2), a process for producing an organogermanium compound represented by the general formula (2-1)

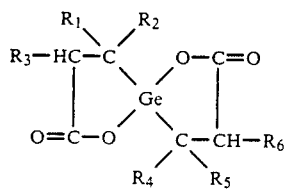

($R_1$ to $R_6$ are independently a hydrogen atom or a lower alkyl group), by lactonizing a compound represented by the general formula (1)

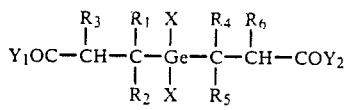

($R_1$ to $R_6$ have the same definitions as given above; X is a halogen atom; and $Y_1$ and $Y_2$ are independently a hydroxyl group or a group chemically equivalent thereto).

The present invention also provides, as a process (the third process of the present invention) for producing the second organogermanium compound of the present invention represented by the general formula (2), a process for producing an organogermanium compound represented by the geneal formula (2-2)

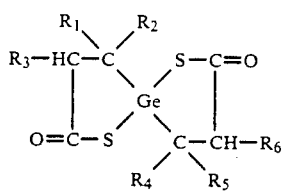

($R_1$ to $R_6$ are independently a hydrogen atom or a lower alkyl group), by lactonizing a compound represented by the general formula (1)

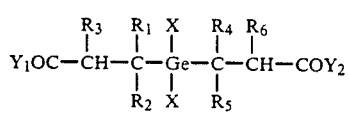

($R_1$ to $R_6$ have the same definitions as given above; X is a halogen atom; and $Y_1$ and $Y_2$ are independently a hydroxyl group or a group chemically equivalent thereto) in the presence of sulfur atoms.

The present invention also provides an agent for inhibiting the activity of opioid peptide-degrading enzyme, which comprises, as an active ingredient, an organogermanium compound represented by the general formula (2)

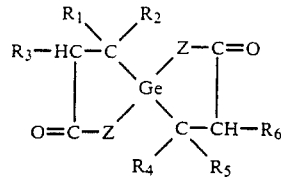

wherein $R_1$ to $R_6$ are independently a hydrogen atom or a lower alkyl group, and Z is an oxygen atom or a sulfur atom.

DETAILED DESCRIPTION OF THE INVENTION

Firstly, the first organogermanium compound of the present invention is described. As understood from the general formula (1), the first organogermanium compound consists of a germanium atom, two halogen atoms X and the following two propionic acid residues,

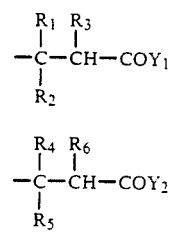

with the two halogen atoms and the two propionic acid residues bonding to the germanium atom.

In the propionic acid residues, the substituents $R_1$ to $R_6$ are independently a hydrogen atom or a lower alkyl group such as methyl, ethyl, propyl, butyl or the like. Of these substituents, $R_1$, $R_2$, $R_4$ and $R_5$ each bond to the 1-position carbon, and $R_2$ and $R_6$ each bond to the 2-position carbon, viewed from the germanium atom.

As a matter of course, $R_1$ to $R_6$ may be the same or different.

In the propionic acid residues, the substituents $Y_1$ and $Y_2$ are each a hydroxyl group, or a group chemically equivalent thereto, such as O-lower alkyl, amino, $O^-M^+$ or the like, which can be converted to a hydroxyl group by a chemical reaction.

As a matter of course, $Y_1$ and $Y_2$ may be the same or different.

The first organogermanium compound of the present invention can be produced by, for example, the first process of the present invention described below.

That is, firstly, a compound represented by the general formula (3)

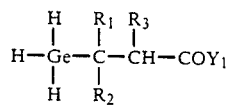

($R_1$ to $R_3$ are independently a hydrogen atom or a lower alkyl group, and $Y_1$ is a hydorxyl group or a group chemically equivalent thereto) is reacted with a halogen $X_2$ to obtain a
dihalide compound represented by the general formula (4)

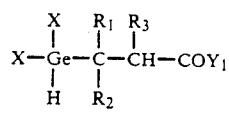

(R₁ to R₃ and Y₁ have the same definitions as given above, and X is a halogen atom).

The above reaction is effected by, for exmaple, dissolving the compound (3) in an appropriate solvent and then dropwise adding a halogen to the solution.

Next, the dihalide compound (4) is reacted with an unsaturated compound represented by the general formula (5)

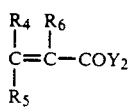

(R₄ to R₆ are independently a hydrogen atom or a lower alkyl group, and Y₂ is a hydroxyl group or a group chemically equivalent thereto) to obtain a compound (1) of the present invention.

The above reaction is effected by, for example, reacting the dihalide compound (4) with the unsaturated compound (5) in the presence of an appropriate solvent or without using any solvent.

The first process of the present invention contains a relatively large number of steps. Therefore, it is not necessary to isolate a desired product in each step and the reaction mixture may be used as it is, in the subsequent step. The first organogermanium compound of the present invention obtained thus is particularly useful as an intermediate for producing the seocnd organogermanium compound of the present invention described later.

Incidentally, the compound (3) can be produced by reducing a trihalide compound represented by the following general formula

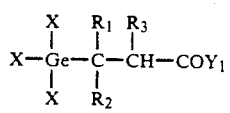

or a corresponding sesquioxide compound represented by the following general formula

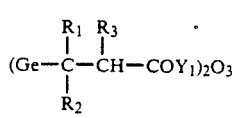

with a reducing agent (e.g. sodium boron hydride NaBH₄)

The second organogermanium compound of the present invention is described. This compound which is represented by the following general formula (2)

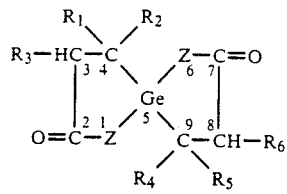

(the numerals 1 to 9 each show a position), has a basic skeleton constituted by a germanium atom as a spiro-atom and two cyclic components

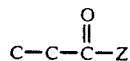

bonding to the germanium atom.

As is clear from the formula (2), the substituents R₃ and R₆ bond to the 3- and 8-postion carbons, respectively; the substituents R₁ and R₂ and the substituents R₄ and R₅ bond to the 4- and 9-positon carbons, respectively. The substituents R₁ to R₆ are independently a hydrogen atom or a lower alkyl group such as methyl, ethyl, propyl, butyl or the like. As a matter of course, similarly in the case of the compound (1), the substituents R₁ to R₆ may be the same or different.

In the formula (2), the 2- and 7-position carbons each take a carbonyl form, and the 1- and 6-postions are each taken by Z. Since this Z is an oxygen atom or a sulfur atom, the second organogermanium compound of the present invention can be classified into two types, i.e. a lactone type represented by the following general formula (2-1) and a thiolactone type represented by the following general formula (2-2).

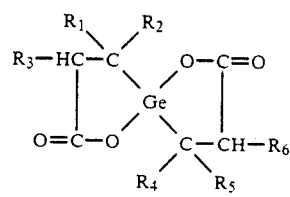

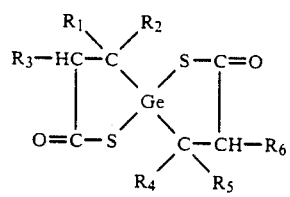

The compound of the present invention represented by the general formula (2-2), when being in water, takes a form represented by the following general formula

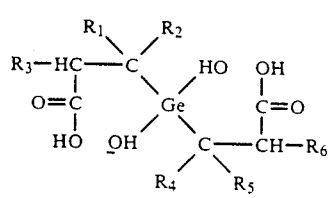

and accordingly it presumed to be easily converted to a corresponding metal salt.

The second organogermanium compound of the present invention can be produced according to, for example, the process shown below.

That is, the organogermanium compound represented by the general formula (2-1) can be obtaiend by the second process of the present invention comprising lactonizing the first organogermanium compound (1) of the present invention.

This cyclization reaction proceeds in an appropriate solvent in the presence of a base such as triethylamine or the like.

The organogermanium compound represented by the general formula (2-2) can be obtained by the third process of the present invention comprising lactonizing the first organogermanium compound (1) of the present invention in the presence of sulfur atoms. This cyclization reaction is effected in an appropriate solvent in the presence of a base such as pyridine or the like, using a sulfur atom donor such as $H_2S$ gas or the like.

In any of the second and third processes, when the $Y_1$ and $Y_2$ of the first organogermanium compound of the present invention are each a group chemically equivalent to a hydroxyl group, the lactonization is effected after the $Y_1$ and $Y_2$ have been converted to a hydroxyl group.

The second organogermanium compound of the present invention obtained thus has a unique structure conatining a germanium atom in the form of a spiro-atom, and accordingly was examined for its properties. As a result, the second organogermanium compound of the present invention showed high oxidation resistance and an inhibitory activity to opioid peptide-degrading enzyme which degrades and deactivates endogenous morphine-like substances (opioid peptide) in living body, such as Enkephaline and the like. Consequently, the applicability of the second organogermanium compound of the present invention as an antihypertensive drug has been confirmed.

The present invention is hereinafter described in more detail by way of Examples.

The compounds (1), (2-1) and (2-2) other than those mentioned in Examples 1-3 can also be synthesized in the substantially same processes.

EXAMPLE 1

Synthesis of compound (1) of present invention (A) Synthesis of compound (3)

(a) 50.88 g (0.15 mol) of 2-carboxyethylgermanium sesquioxide was added to 500 ml of water. The solution was made alkaline with potassium hydroxide. To the alkaline solution was added 22.7 g (0.60 mol) of sodium boron hydride. The mixture was stirred for 30 minutes and then made acidic with acetic acid. The acidic mixture was extracted with ethyl acetate (250 ml×2). The extracts were combined and dried with anhydrous sodium sulfate. The solvent was removed by distillation to obtain a colorless transparent oily substance. The substance was subjected to vacuum distillation to obtain, as a colorless transparent fraction of 68° C./3 mmHg, 31.1 g (69.8%) of 3-(trihydrogermyl)propionic acid which is a compound of the general formula (3) wherein $R_1 = R_2$ TM $R_3 = H$ and $Y_1 = OH$.

Elemental analysis, wt. %

Calc. for $GeC_3H_8O_2$ Ge 48.82, C 24.23, H 5.42,

Found: Ge 48.69, C 24.31, H 5.40.

IR γ KBr/max cm$^{-1}$: 2070 (Ge-H), 1790 (C=O),

NMR (CDCl$_3$) δ: 1.28 (2H,m,Ge—CH$_2$), 2.53 (2H,t,CH$_2$—CO), 3.56 (3H,t,Ge-H ), 10.80 (lH,s,COOH), (b) 79.83 g (0.30 mol) of 3-trichlorogermylbutanoic acid was added to water. The solution was made alkaline with potassium hydroxide. To the alkaline solution was added 22.7 g (0.60 mol) of sodium boron hydride. The mixture was stirred for 30 minutes and then made acidic with acetic acid. The acidic mixture was extracted with ethyl acetate (250 ml×2). The extracts were combined and dried with anhydrous sodium sulfate. The solvent was removed by distillation to obtain a yellow oily substance. The substance was subjected to vacuum distillation to obtain, as a colorless transparent fraction of 71° C/2 mmHg, 36.79 g (75.4%) of 3-(trihydrogermyl)butanoic acid which is a compound of the general formula (3) wherein $R_1 = CH_3$, $R_2$ TM $R_3 = H$ and $Y_1 = OH$.

Elemental analysis, wt. %

Cal. for $GeC_4H_{10}O_2$: Ge 44.61, C 29.53, H 6.19,

Found: Ge 44.50, C 29.51, H 5.99.

IR γ KBr/max cm$^{-1}$: 2060 (Ge-H), 1705 (C=O).

1.87 (lH,m,Ge—CH)

2.51 (2H,d,CH$_2$—CO), 3.63 (3H,d,Ge-H$_3$), 11.69 (1H,s,COOH).

(B) Synthesis of compound (1)

(a) 7.43 g (0.05 mol) of 3-(trihydrogermyl)propionic acid was dissolved in 100 ml of chloroform. Thereto was added 15.98 g (0.10 mol/10 ml chloroform) of bromine with cooling with dry ice-acetone. The mixture was returned to room temperature. The solvent was removed by distillation to obtain, as white crystals, 3-(dibromohydrogermyl)propionic acid which is a compound of the general formula (4) wherein $R_1 = R_2 = R_3 = H$, X=Br and $Y_1$ TM OH.

To the crystals was added 10.8 g (0.15 mol) of acrylic acid which is a compound of the general formula (5) wherein $R_4 = R_5$ TM $R_6 = H$ and $Y_2 = OH$. The mixture was stirred and a reaction took place with violent heat generation. Stirring was continued for 2.5 hours. Acrylic acid was removed by distillation under vacuum. To the residue was added 50 ml of concentrated hydrochloric acid, and the mixture was stirred. The resulting white crystals were recrystallized from concentrated hydrochloric acid (there occurred substitution with halogen) to obtain, as colorless transparent crystals, 8.62 g (59.5%) of dichlorobis(1-0methyl-2-carboxyethyl) germone which is a compound of the general formula (1) whereiı: $R_1 = R_2$ TM $R_3 = R_4 = R_5 = R_6 = H$, X=Cl and $Y_1$ T- M $Y_2$ TM OH.

Melting point: 106°-107° C.

Elemental analysis, wt.%

Cal. for $Ge_6H_{10}O_4Cl_2$: Ge 25.06, C 24.88, H 3.48, Cl 24.48,

Found: Ge 25.10, C 25.02, H 3.47, Cl 24.72

IR δ KBr/max cm$^{-1}$: 1695 (C=O), 390 (Ge-Cl),

NMR (CDCl$_3$+CD$_3$OD) δ: 1.97 (4H,t,Ge(—CH$_2$)$_2$), 2.77 (4H,t,(CH$_2$—CO)$_2$).

(b) 8.13 g (0.05 mol) of 3-(trihydrogermyl)butanoic acid was dissolved in 100 ml of chloroform. Thereto was added 15.98 g (0.10 mol/10 ml chloroform) with cooling with dry ice-acetone. The mixture was returned to room temperature. The solvent was removed by distillation to obtain, as white crystals, 3-(dibromohydrogermyl)butanoic acid which is a compound of the general formula (4) wherein $R_1=CH_3$, $R_2=R_3=H$, $X=Br$ and $Y_1=OH$.

To the crystals were added 10 ml of ethyl ether and 4.30 g (0.05 mol) of crotonic acid which is a compound of the general formula (5) wherein $R_4=CH_3$, $R_5=R_6=H$ and $Y_2=OH$. The mixture was refluxed for 5 hours with heating. The solvent was removed by distillation. The resulting white crystals were washed with n-hexane and then recrystallized from concentrated hydrochloric acid (there occurred substitution with halogen) to obtain, as colorless transparent crystals, 9.19 g (57.9%) of dichlorobis(10methyl-2-carboxyethyl)germane which is a compound of the general formula (1) wherein $R_1=R_4=CH_3$, $R_2=R_3=R_5=R_6=H$, $X=Cl$ and $Y_1=Y_2=OH$.

Melting point: 100°-101° C.
Elemental analysis, wt. %
Calc for $GeC_8H_{14}O_4Cl_2$ Ge 22.85, C 30.25, H 4.44, Cl 22.32,
Found: Ge 22.92, C 30.19, H 4.41, Cl 22.17.
IR $\gamma$ KBr/max cm$^{-1}$: 1700 (C=O),
380, 355 (Ge-Cl),
NMR (CDCl$_3$ CD$_3$OD) $\delta$:1.32 (6H,d,(C—CH$_3$($_2$),
2.40 (2H,sext,Ge(—CH)$_2$), 2.70 (4H,m,(CH$_2$—CO)2).

(c) 16.26 g (0.10 mol) of 2-methyl-3-(trihydrogermyl)-propionic acid was dissolved in 150 ml of chloroform. Thereto was added 31.96 g (0.20 mol/20 ml chloroform) of bromine with cooling with dry ice-acetone. The mixture was returned to room temperature. The solvent was removed by distillation to obtain, as a slightly yellow oily substance, 2-methyl-3-(dibromohydrogermyl)propionic acid which is a compound of the general formula (4) wherein $R_1=R_2=H$, $R_3=CH_3$, $X=Br$ and $Y_1=OH$. (This substance crystallized when cooled under vacuum.)

To the substance were added 10 ml of ethyl ether and 8.6 g (0.10 mol) of methacrylic acid which is a compound of the general formula (5) wherein $R_4=R_5=H$, $R_6$ TM CH$_3$ and $Y_2=OH$. Immediately, heat generation took place and the reaction mixture got cloudy. Stirring was effected for 30 minutes. The solvent was removed by distillation. The resulting white crystals were washed with n-hexane and then recrystallized from concentrated hydrochloric acid (there occurred substitution with halogen) to obtain, as colorless transparent crystals, 15.68 g (49.4%) of dichlorobis(2-carboxypropyl)germane which is a compound of the general formula (1) wherein $R_1=R_2=R_4=R_5$ TM H, $R_3=R_6=CH_3$, $X=Cl$ and $Y_1=Y_2=OH$.

Melting point = 107°-108° C.,
Elemental analysis, wt. %
Calc. for $GeC_8H_{14}O_4Cl_2$ Ge 22.85, C 30.25, H 4.44, Cl 22.32,
Found: Ge 23.01, C 30.00, H 4.38, Cl 22.14.
IR $\gamma$ KBr/max cm$^{-1}$: 1690 (C=O),
375, 350 (Ge—Cl).
NMR (CDCl$_3$+CD$_3$OD) $\delta$: 1.33 (6H,d,(C—CH$_3$)$_2$),
2.00 (4H,m,Ge(—CH$_2$)$_2$),
3.03 (2H,m,(CH—CO)$_2$).

(d) 8.83 g (0.05 mol) of 2-methyl-3-(trihydrogermyl)-butanoic acid was dissolved in 100 ml of chloroform. Thereto was added 15.98 g (0.10 mol/10 ml chloroform) of bromine with cooling with dry ice-acetone. The mixture was returned to room temperature. The solvent was removed by distillation to obtain, as white crystals, 2-methyl-3-(dibromohydrogermyl)butanoic acid which is a compound of the general formula (4) wherein $R_1=R_3=CH_3$, $R_2$ TM H, X TM Br and $Y_1=OH$.

To the crystals were added 5 ml of ethyl ether and 5.00 g (0.05 mol) of 2-methylcrotonic acid which is a compound of the general formula (5) wherein $R_4=R_6=CH_3$, $R_5=H$ and $Y_2=OH$. The mixture was subjected to a reaction for 40 minutes at room temperature and then for 1 hour with heating. The solvent was removed by distillation. The resulting crystals were dissolved in ethyl acetate, followed by addition of n-hexane for recrystallization to obtain, as colorless transparent crystals, 15.68 g (49.4%) of dichlorobis(1-methyl-2-carboxypropyl)germane which is a compound of the general formula (1) wherein $R_1=R_3=R_4=R_6=CH_3$, $R_2=R_5=H$, $X=Br$ and $Y_1=Y_2=OH$.

Melting point: 188°-189° C.
Elemental analysis, wt. %
Calc. for $GeC_{10}H_{18}O_4Br_2$: 16.70, C 27.63, H 4.17, Br 36.77;
Found: Ge 16.65, C 27.51, H 4.01, Br 36.72
IR $\gamma$ KBr/max cm$^{-1}$: 1680 (C=O),
NMR (CDCl$_3$) $\gamma$: 1.28 (12H,m,(—CH$_3$)$_4$),
2.42 (2H,m,Ge(—CH)$_2$),
3.01 (2H,m,(CH—CO)$_2$).

EXAMPLE 2

Synthesis of compound (2-1) of present invention (a) In 100 ml of ethyl ether was dissolved 2.90 g (0.01 mol) of dichlorobis(2-carboxyethyl)germane which is a compound of the general formula (1) wherein $R_1=R_2=R_3=R_4=R_5=R_6=H$, $X=Cl$ and $Y_1=Y_2=OH$. Thereto was added 2.02 g (0.02 mol) of triethylamine with ice cooling. The resulting crystals were collected by filtration and then heated to 130°-150° C. under vacuum to sublimate and remove the salt of triethylamine. The residue was washed with acetone to obtain, as white crystals, 1.99 g (91.9%) of a compound of the general formula (2-1) wherein $R_1=R_2$ TM $R_3$ TM $R_4=R_5=R_6=H$ Melting point: 325° C. (decomposed).
Elemental analysis, wt. %
Calc. for $GeC_6H_8O_4$: Ge 33.50, C 33.25, H 3.72,
Found: Ge 33.40, C 33.29, H 3.93,
IR $\gamma$ KBr/max cm$^{-1}$ 1700, 1625 (C=O)
NMR (D$_2$O) $\delta$: 1.65 (4H,t,Ge(—CH$_2$)$_2$),
2.70 (4H,t,(CH$_2$—CO)$_2$) , (b) In 100 ml of ethyl ether was dissolved 3.18 g (0.01 mol) of dichlorobis(1-0methyl-2-carboxyethyl)germane whichis a compound of the general formula (1) wherein $R_1=R$ , $R_2=R_3=R_5=R_6=H$, $X=Cl$ and $Y_1=Y_2=OH$. Thereto was added 2.02 g (0.02 mol) of triethylamine with ice cooling. The resulting crystals were collected by filtration and then heated to 130°-150° C. under vacuum to sublimate and remove the salt of triethylamine. The residue was washed with acetone to obtain, as white crystals, 1.95 g (79.7%) of a compound of the general formula (2-1) wherein $R_1=R_4=CH_3$ and $R_2=R_3=R_5=R_6=H$.

Melting point: 277° C. (decomposed).
Elemental analysis, wt. %
Calc. for $GeC_8H_{12}O_4$: Ge 29.66, C 39.26, H 4.94,
Found: Ge 29.73, C 39.17, H 4.89,
IR $\gamma$ KBr/max cm$^{-1}$: 1695, 1620 (C=O),
NMR (D$_2$O) $\delta$: 1.18, 1.27 (6H,d,(—CH$_3$)$_2$), 2.13 (2H,m,Ge(—CH)$_2$),
2.43, 2.98 (4H,dd,(CH$_2$—CO)$_2$).

(c) In 100 ml of ethyl ether was dissolved 3.18 g (0.01 mol) of 3,3'-(dichlorogermyl)-2-methylpropanedioic acid which is a compound of the general formula (1) wherein $R_1=R_2=R_4=R_5=H$, $R_3=R_6=CH_3$, $X=Cl$ and $Y_1=Y_2=OH$. Thereto was added 2.02 g (0.02 mol) of triethylamine with ice cooling. The resulting crystals were collected by filtration and then heated to 130°–150° C. under vacuum to sublimate and remove the salt of triethylamine. The residue was washed with acetone to obtain, as white crystals, 2.13 g (79.7%) of a compound of the general formula (2-1) wherein $R_1=R_2=R_4=R_5=H$ and $R_3=R_6=CH_3$.

Melting point: 310° C. (decomposed).
Elemental analysis, wt. %
Calc. for GeC$_8$H$_{12}$O$_4$: Ge 29.66, C 39.26, H 4.9,
Found: Ge 29.77, C 39.16, H 4.94.
IR γ KBr/max cm$^{-1}$: 1685, 1610 (C=O).
NMR (D$_2$O) δ: 1.30 (6H.d.(CO—C—CH$_3$)2),
1.40 1.88 (4H.m,(Ge—CH$_2$)2),
2.92 (2H,m,(CH—CO)$_2$).

(d) In 50 ml of ethyl ether was dissolved 1.74 g (0.004 mol) of dibromobis(1-methyl-2-carboxypropyl)germane which is a compound of the general formula (1) wherein $R_1=R_3=R_4=R_6=CH_3$, $R_2=R_5=H$, $X=Br$ and $Y_1=Y_2=OH$. Thereto was added 0.81 g of triethylamine with ice cooling. The resulting crystals were collected by filtration and then heated to 130°–150° C. under vacuum to sublimate and remove the salt of triethylamine. The residue was washed with acetone to obtain, as white crystals, 0.70 g (65.4%) of a compound of the general formula (2-1) wherein $R_1=R_3=R_4=R_6=CH_3$ and $R_2=R_5=H$.

Melting point: 276° C. (decomposed).
Elemental analysis, wt. %
Calc. for GeC$_{10}$H$_{16}$O$_4$: Ge 26.61, C 44.02, H 5.91,
26.67, C 44.06, H 5.91.
γ KBr/max cm$^{-1}$ 1690, 1615 (C=O).
NMR (D$_2$O) δ: 1.26 (12H,m,(CH$_3$—CH—CH—CH$_3$)2),
1.77 (2H,m,Ge(—CH)2),
2.51 (2H,m,(CH—CO)2),

EXAMPLE 3

Synthesis of compound (2-2) of present invention (a) 50 ml of thionyl chloride was added to 5.79 g (0.02 mol) of dichlorobis(2-carboxyethyl)germane which is a compound of the general formula (1) wherein $R_1=R_2=R_3=R_4=R_5=R_6=H$, $X=Cl$ and $Y_1=Y_2=OH$. The mixture was refluxed for 1 hour with heating. Excessive thionyl chloride was removed by distillation to obtain a corresponding acid chloride quantitatively.

4.90 g (0.015 mol) of this acid chloride was dissolved in 200 ml of acetone. H$_2$S gas was passed therethrough and 4.74 g (0.06 mol) of pyridine was added, with ice cooling. The mixutre was stirred for 30 minutes. The resulting crystals were removed by filtration. The filtrate was subjected to distillation to remove the solvent to obtain crystals. The crysals were washed with 100 ml of water and then extracted with ethyl acetate. The extract was dried with anhydrous sodium sulfate and then subjected to distillation to remove ethyl acetate to obtain crystals. The crystals was purified by sublimation to obtain, as white crystals, 2.60 g (69.7%) of a compound of the general formula (2-2) wherein $R_1=R_2=R_3=R_4=R_5=R_6=H$.

Melting point: 116°–117° C.
Elemental analysis, wt. %
Calc. for GeC$_6$H$_8$O$_2$S$_2$: Ge 29.17, C 28.96, H 3.24, S 25.77,
Found: Ge 29.12, C 29.05, H 3.23, S 25.51.
IR γ KBr/max cm$^{-1}$: 1670 (C=O),
360 (Ge-S),
NMR (CDCl$_3$) δ: 2.13 (4H,m,Ge(—CH$_2$)$_2$),
2.93 (4H,m,(CH$_2$—CO)$_2$).

(b) 50 ml of thionyl chloride was added, to 6.35 g (0.02 mol) of dichlorobis(methyl)2-carboxyethyl)germane which is a compound of the general formula (1) wherein $R_1=R_4=CH_3$, $R_2=R_3=R_5=R_6=H$, $X=Cl$ and $Y_1=Y_2=OH$. The mixture was refluxed for 3.5 hours with heating. Excessive thionyl chloride was removed by distillation to obtain a corresponding acid chloride quantitatively.

5.32 g (0.015 mol) of this acid chloride was dissolved in 100 ml of acetone. H$_2$S gas was passed therethrough and 4.74 g (0.06 mol) of pyridine was added, with ice cooling. The mixture was stirred for 30 minutes. The resulting crystals were removed by filtration. The filtrate was subjected to distillation to remove the solvent to obtain crystals. The crystals were washed with 100 ml of water and then extracted with ethyl acetate. The extract was dried with anhydrous sodium sulfate and then subjected to distillation to remove ethyl acetate to obtain crystals. The crystals were purified by sublimation to obtain, as white crystals, 2.13 g (51.3%) of a compound of the general formula (2-2) wherein $R_1=R_4=CH_3$ and $R_2=R_3=R_5=R_6=H$.

Melting point: 101°–103° C.
Elemental analysis, wt. %
Calc. for GeC$_8$H$_{12}$O$_2$S$_2$: Ge 26.22, C 34.70, H 4.37, S 23.16
Found: Ge 26.29, C 34.77, H 4.31, S 22.96.
IR γ KBr/max cm$^{-1}$ 1685 (C=O).
NMR (CDCl$_3$) δ: 1.40 (6H,m,(—CH$_3$)$_2$),
2.20-3.27 (6H,m,Ge(—CH—CH$_2$)$_2$).

(c) 50 ml of thionyl chloride was added to 6.35 g (0.02 mol) of dichlorobis(2-0carboxypropyl)germane which is a compound of the general formula (1) wherein $R_1=R_2=R_4=R_5=H$, $R_3=R_6=CH_3$, $X=Cl$ and $Y_1=Y_2=OH$. The mixture was refluxed for 3 hours with heating. Excessive thionyl chloride was removed by distillation to obtain a corresponding acid chloride quantitatively.

5.32 g (0.015 mol) of this acid chloride was dissolved in 200 ml of acetone. H$_2$S gas was passed therethrough and 4.74 g (0.06 mol) of pyridine was added, with ice cooling. The mixture was stirred for 30 minutes. The resulting crystals were removed by filtration. The filtrate was subjected to distillation to remove the solvent to obtain crystals. The crystals were washed with 100 ml of water and then extracted with ethyl acetate. The extract was dried with anhydrous sodium sulfate and then subjected to distillation to remove ethyl acetate to obtain crystals. The crystals were purified by sublimation to obtain, as white crystals, 2.43 g (58.5%) of a compound of the general formula (2-2) wherein $R_1=R_2=R_4=R_5=H$ and $R_3=R_6=CH_3$.

Melting point: 104°–106° C.
Elemental analysis, wt. %
Calc. for GeC$_8$H$_{12}$O$_2$S$_2$: Ge 26.22, C 34.70, H 4.37, S 23.16,
Found: Ge 26.11, C 34.61, H 4.32, S 23.01.
IR γ KBr/max cm$^{-1}$: 1685 (C=O),
NMR (CDCl$_3$) δ: 1.30 (6H,m,(CO—C—CH$_3$)$_2$),
1.83, 2.27 (4H,m,Ge(—CH$_2$)$_2$,
3.00 (2H,m,(CO—CH)$_2$).

(d) 50 ml of thionyl chloride was added to 8.69 g (0.02 mol) of dibromobis(1-methyl-2-0carboxypropyl)germane which is a compound of the general formula (1) wherein R$_1$=R$_3$=R$_4$=R$_6$=CH$_3$, R$_2$=R$_5$=H, X=Br and Y$_1$=Y$_2$=OH. The mixture was refluxed for 2 hours with heating. Excessive thionyl chloride was removed by distilation to obtain a corresponding acid chloride.

5.74 g (0.015 mol) of this acid chloride was dissolved in 100 ml of acetone. H$_2$S gas was passed therethrough and 4.74 g (0.06 mol) of pyridine was added, with ice cooling. The mixture was stirred for 30 minutes. The resulting crystals were removed by filtration. The filtrate was subjected to distillation to remove the solvent to obtain crystals. The crystals were washed with ethanol. The insoluble matter was removed by filtration. Purification by sublimation was effected to obtain, as white crystals, 0.98 g (21.4%) of a compound of the general formula (2-2) wherein R$_1$=R$_3$=R$_4$=R$_6$=CH$_3$ and R$_2$=R$_5$=H.

Melting point: 120°-125° C.,
Elemental analysis, wt. %
Calc. for GeC$_{10}$H$_{16}$O$_2$S$_2$: Ge 23.80, C 39.39, H 5.29, S 21.03,
Found: Ge 23.59, C 39.51, H 5.12, S 20.87,
IR γ KBr/max cm$^{-1}$: 1700 (C=O),
NMR (CDCl$_3$)δ: 1.21 (6H,d,Ge(C—CH$_3$)$_2$),
1.29 (6H, d,(CO—C—CH$_3$)2),
2.47 (2H,quint,Ge(—CH$_2$)$_2$),
2.95 (2H,quint, (CO—CH)$_2$).

EXAMPLE 4

In order to examine the utility of the compound (2) of the present invention, the compounds (2-1) synthesized in Example 2 were measured for inhibitory activity for opioid peptide-degrading enzyme. As a result, all of the compounds (2-1) obtained in Example 2 showed a significant inhibitory activity. Their activities were as strong as 60-80% (40-70 μg in terms of IC50) to dipeptidylaminopeptidase derived from simian brain.

Also, some of the compounds (2-1) were measured for inhibitory activity to angiotensin-converting enzyme (ACE-I) which is an opioid peptide-degrading enzyme, according to the following test.

That is, 20 μl of a solution containing 1.4 ng of a converting enzyme obtaiend from porcine kidney was mixed with 50 μl of a test solution containing 5 mg/ml of one of the compounds (2-1) of the present invention shown below. The mixture was allowed to stand for 5 minutes. Thereto was added 240 μl of a substrate solution (a solution of Hippuryl-His-Leu). The resulting mixture was shaked for 1 hour at 37° C. for reaction. 1.5 ml of an aqueous 0.28 N NaOH solution was added to terminate the enzymatic reaction. Then, there was added 100 μl of a solution of 2% of o-phthalaldehyde dissolved in methanol. After exactly 10 minutes, 3 N hydrochloric acid was added to terminate the fluorescent reaction. The resulting mixture was diluted tenfold. The diluted mixture was measured by fluorescent method at an excitation wavelength of 340 nm and a fluorescent wavelength of 455 nm. The measurement of each sample was conducted by tripple tests and the measurement of the background was conducted by double tests.

| Test compound (2-1) | Substituents in general formula (2-1) |
|---|---|
| 1 | R$_1$ = R$_2$ = R$_3$ = R$_4$ = R$_5$ = R$_6$ = H |
| 2 | R$_1$ = R$_2$ = R$_4$ = R$_5$ = H, R$_3$ = R$_6$ = CH$_3$ |
| 3 | R$_1$ = R$_3$ = R$_4$ = R$_6$ = H, R$_2$ = R$_5$ = CH$_3$ |
| 4 | R$_1$ = R$_3$ = R$_4$ = R$_6$ = CH$_3$, R$_2$ = R$_5$ = H |

The results are shown in the following table. In the table, an inhibition (%) of, for example, 0.2 indicates that 99.8% of the enzyme used was inhibited.

| Test compound (2-1) | Inhibition (%) |
|---|---|
| 1 | 0.7 |
| 2 | 0.1 |
| 3 | 0.2 |
| 4 | 0.2 |

For reference, opioid peptide and its degrading enzymes are described in detail in, for example, Japanese Patent Publication Nos. 44168/1989 and 44169/1989.

Reference Example

In order to examine other utility of the compound (2) of the present invention, the compounds (2-2) synthesized in Example 3 were measured for anti-oxidation activity. In the measurement, there was used an oxidative color-developing system utilizing o-phenylenediamine. Anti-oxidation activity was rated by measuring the increase in absorbancy of said system. As a result, the above compounds (2-2) showed singnificant antioxidancy at a low concentration of 0.003-0.03 mM.

As described above, the present invention provides useful organogermanium compounds and processes for producing said compounds.

What is claimed is:

1. An organogermanium compound represented by the formula

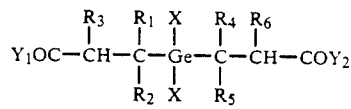

wherein R$_1$ to R$_6$ are independently a hydrogen atom or a lower alkyl group; X is a halogen atom; and Y$_1$ and Y$_2$ are independently a hydroxyl group or a group which can be chemically converted to a hydroxy group.

2. An organogermanium compound represented by the formula

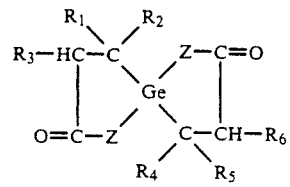

wherein R$_1$ to R$_6$ are independently a hydrogen atom or a lower alkyl group, and Z is an oxygen atom or a sulfur atom.

3. An organogermanium compound according to claim 2, wherein Z is an oxygen atom.

4. An organogermanium compound according to claim 2, wherein Z is a sulfur atom.

5. A process for producing an organogermanium compound represented by the formula

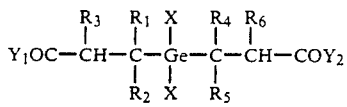

wherein $R_1$ to $R_6$ are independently a hydrogen atom or a lower alkyl gruop; X is a halogen atom; and $Y_1$ and $Y_2$ are independently a hydroxyl group or a group which can be chemically converted to a hydroxyl group, which process comprises reacting a compound represented by the formula

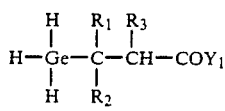

wherein $R_1$ to $R_3$ and $Y_1$ have the same definitions as given above, with a halogen $X_2$ to obtain a dihalide compound represented by the formula

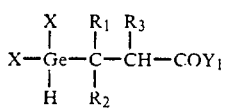

wherein $R_1$ or $R_3$ and $Y_1$ have the same definitions as given above, and X is a halogen atom, and reacting the diahlide compound with an unsaturated compound represented by the formula

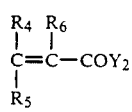

wherein $R_4$ and $R_6$ and $Y_2$ have the same definitions as given above, to obtain said organogermanium compound.

6. A process for producing an organogermanium compound represented by the formula

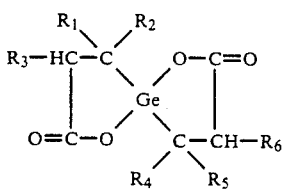

wherein $R_1$ to $R_6$ are independently a hydrogen atom or a lower alkyl group, by lactonizing a compound represented by the formula

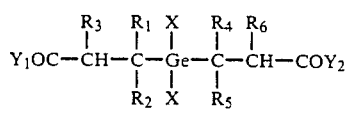

wherein $R_1$ to $R_6$ have the same definitions as given above; X is a halogen atom; $Y_1$ and $Y_2$ are independnetly a hydroxyl gruop or a gorup which an be chemically converted to a hydroxyl group.

7. A process according to claim 6, wherein when $Y_1$ and $Y_2$ are both a group which can be chemically converted to a hydroxyl group, the lactonization is effected after the $Y_1$ and $Y_2$ have been converted to a hydroxyl group.

8. A process for producing an organogermanium compound represented by the formula

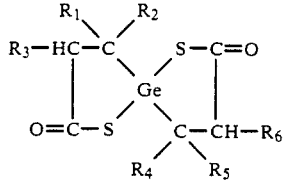

wherein $R_1$ to $R_6$ are independently a hydrogen atom or a lower alkyl group, by lactonizing a compound represented by the formula

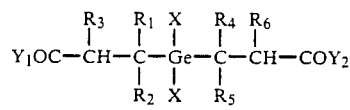

wherein $R_1$ to $R_6$ have the same definitions as given above; X is a halogen atom; $Y_1$ and $Y_2$ are independnetly a hydroxyl group or a group which an be chemically converted to a hydroxyl group, in the presence of sulfur atoms.

9. A process according to claim 8, wherein when $Y_1$ and $Y_2$ are both a group which can be converted to a hydroxyl group, the lactonization is effected in the presence of sulfur atoms after the $Y_1$ and $Y_2$ have been converted to a hydroxyl group.

10. An agent for inhibiting the activity of opioid peptide-degrading enzyme, which comprises, as an active ingredient, an organogermanium compound represented by the formula

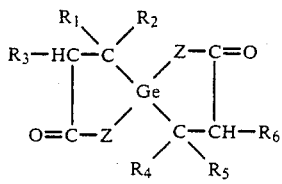

wherein $R_1$ to $R_6$ are independnetly a hydroxyl atom or a lower alkyl group, and Z is an oxygen atom or a sulfur atom.

11. An agent according to claim 10, wherein Z is an oxygen atom.

12. A method of inhibiting the action of an opioid peptide-degrading enzyme, comprising administering to an organism in need of such treatment an effective opioid peptide-degrading enzyme amount of a compound represented by the formula

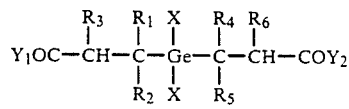

wherein $R_1$ to $R_6$ are independnetly a hydroxyl atom or a lower alkyl group, and Z is an oxygen atom or a sulfur atom.

13. A method according to claim 12, wherein Z is an oxygen atom.

* * * * *